United States Patent [19]  
MacDonald et al.

[11] 4,340,419  
[45] Jul. 20, 1982

[54] S-TRIAZINE HERBICIDAL ANTIDOTES

[75] Inventors: Alan A. MacDonald, Kensington; Ferenc M. Pallos, Walnut Creek; Eugene G. Teach, El Cerrito, all of Calif.

[73] Assignee: Stauffer Chemical Company, Westport, Conn.

[21] Appl. No.: 165,994

[22] Filed: Jul. 7, 1980

[51] Int. Cl.³ ............................................. A01N 25/32
[52] U.S. Cl. ............................................ 71/93; 71/88; 71/100
[58] Field of Search ............................ 71/93, 100, 88

[56] References Cited  
U.S. PATENT DOCUMENTS  
4,220,467  9/1980  Dombay et al. .................. 71/93

Primary Examiner—Catherine L. Mills  
Attorney, Agent, or Firm—Harry A. Pacini

[57] ABSTRACT

Non-phytotoxic antidotally effective amounts of compounds having the formula

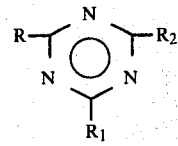

in which
R is selected from the group consisting of haloalkyl having 1-4 carbon atoms and alkylamino having 1-4 carbon atoms;
$R_1$ is selected from the group consisting of alkyl having 1-4 carbon atoms, haloalkyl having 1-4 carbon atoms and chloro; and
$R_2$ is selected from the group consisting of haloalkyl having 1-4 carbon atoms and N-dichloroacetylethylamino protect crops from thiolcarbamate herbicidal injury.

13 Claims, No Drawings

S-TRIAZINE HERBICIDAL ANTIDOTES

BACKGROUND OF THE INVENTION

A herbicide is a compound which controls or modifies plant growth, e.g., killing, retarding, defoliating, desiccating, regulating, stunting, tillering, stimulating, and dwarfing. "Plant" refers to all physical parts, including seeds, seedlings, saplings, roots, tubers, stems, stalks, foliage, and fruits. "Plant growth" is meant to include all phases of development from seed germination to natural or induced cessation of life.

Herbicides are generally used to control or eradicate undesirable vegetation. They have gained a high degree of commercial success because it has been shown that such control can increase crop yield and reduce harvesting costs.

Herbicidal effectiveness is dependent upon several variables. One of these is the time or growth related method of application. The most popular methods of application include: pre-plant incorporation into the soil; pre-emergence surface treatment of seeded soil; and post-emergence treatment of the plant and soil.

The most important determinant of herbicidal effectiveness is the susceptibility of the beneficial crop and selectivity toward weeds. Certain herbicidal compounds are phytotoxic to some weed species but not to others.

A manufacturer of a herbicide generally recommends a range of rates and concentrations calculated to maximize weed control. The range of rates varies from approximately 0.01 to 50 pounds per acre (lb/A) (0.0112 to 56 kilograms per hectare (k/ha)), usually from 0.1 to 25 lb/A (0.112 to 28 k/ha). The actual amount used depends upon several considerations, including, crop tolerance, particular weed susceptibility and overall cost limitations.

Some herbicides display exclusive selectivity toward weed species. Many are toxic to both weeds and the intended crop beneficiary. Therefore, a particular herbicide may proscribe its injurious effect on the cultivated crop even though it may otherwise provide excellent control of weeds found in the crop field.

To preserve the beneficial aspects of herbicide use and to mitigate crop damage, many herbicidal antidotes have been prepared. These antidotes reduce or eliminate damage to the crop without substantially impairing the beneficial effect of the herbicide. See U.S. Pat. Nos. 4,021,224, 4,021,229 and Belgian Pat. No. 846,894.

Although several explanatory theories have been advanced, the precise mechanism by which an antidote reduces herbicidal crop injury while retaining weed injury has not been conclusively established. An antidote compound may in fact be a remedy, interferent, protectant, or antagonist. As used herein, "antidote" describes a compound which has the effect of establishing herbicidal selectivity or herbicidal phytotoxicity toward weed species and reduced or non-phytotoxicity to cultivated crop species.

As an alternative mode of action, the compounds of this invention may interfere with the normal herbicidal action of the thiolcarbamate-type herbicides to render them selective in their action. Whichever mode of action is present, the corresponding beneficial and desirable effect is the continued herbicidal effect of the thiolcarbamate with the accompanying decreased herbicidal effect on desired crop species. This advantage and utility will become more apparent hereinafter.

Therefore, the terms herbicide antidotes or antidotal amount is meant to describe that effect or the amount which produces the effect which tends to counteract the normal injurious herbicidal response that the herbicide might otherwise produce. Whether it is to be termed a remedy, interferent, protectant, or the like, will depend upon the exact mode of action. The mode of action is varied, but the effect, which is desirable, is the result of the method of treating the soil in which a crop is planted.

Thiolcarbamate herbicides are particularly effective in the control of grassy type weeds which interfere with the cultivation of a wide variety of crops, e.g., barley, corn, lentils, peanuts, peas, potatoes, soybeans, spinach, tobacco and tomatoes. Frequently, the beneficent use of thiolcarbamates requires the addition of an antidote.

DESCRIPTION OF THE INVENTION

It has been discovered that the tolerance of several crops to thiolcarbamate herbicides can be increased by the use of a non-phytotoxic antidotally effective amount of a s-triazine compound of the formula

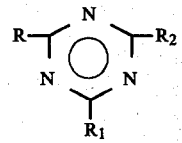

in which

R is selected from the group consisting of haloalkyl having 1–4 carbon atoms, preferably dichloromethyl or trichloromethyl, and alkylamino having 1–4 carbon atoms, preferably ethylamino and propylamino;

$R_1$ is selected from the group consisting of alkyl having 1–4 carbon atoms, preferably methyl, haloalkyl having 1–4 carbon atoms, preferably dichloromethyl, and chloro; and $R_2$ is selected from the group consisting of haloalkyl having 1–4 carbon atoms, preferably dichloromethyl and trichloromethyl, and N-dichloroacetylethylamino.

This invention embodies a two-part herbicidal composition comprising (a) a non-phytotoxic antidotally effective amount of a compound of the formula

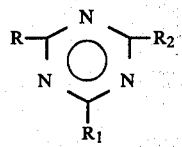

in which

R is selected from the group consisting of haloalkyl having 1–4 carbon atoms, preferably dichloromethyl or trichloromethyl, and alkylamino having 1–4 carbon atoms, preferably ethylamino and propylamino;

$R_1$ is selected from the group consisting of alkyl having 1–4 carbon atoms, preferably methyl, haloalkyl having 1–4 carbon atoms, preferably dichloromethyl, and chloro; and $R_2$ is selected from the group consisting of haloalkyl having 1–4 carbon atoms, preferably dichloromethyl and trichloromethyl, and N-dichloroacetylethylamino.

(b) a herbicidally effective amount of a thiolcarbamate of the formula

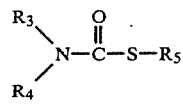

in which

R₃ is selected from the group consisting of alkyl having 1-6 carbon atoms and alkenyl having 2-6 carbon atoms;

R₄ is selected from the group consisting of alkyl having 1-6 carbon atoms, alkenyl having 2-6 carbon atoms, cyclohexyl and phenyl; or R₃ and R₄ together form an alkylene group having 5-10 carbon atoms; and R₅ is selected from the group consisting of alkyl having 1-6 carbon atoms, haloalkyl having 1-4 carbon atoms, cycloalkyl having 5-10 carbon atoms, phenyl, substituted phenyl, wherein the substituents are alkyl having 1-4 carbon atoms, haloalkyl having 1-4 carbon atoms, and halo, benzyl and substituted benzyl, wherein the substituents are alkyl having 1-4 carbon atoms, haloalkyl having 1-4 carbon atoms and halo.

The terms alkyl and alkenyl as used herein are intended to include both straight- and branched-chain groups. The term halo is intended to include mono- and polyhalo groups and includes, chloro, bromo, iodo, fluoro and mixtures thereof. All carbon atom ranges are intended to be inclusive of both upper and lower limits. Exemplary of alkyl are methyl, ethyl, n-propyl, isopropyl, n-butyl, isobutyl, tertiarybutyl, pentyl, hexyl and the like. Exemplary of alkenyl are such groups as vinyl, proenyl, butenyl, pentyl, hexenyl and the like. Exemplary of cycloalkyl are cyclopentyl, cyclohexyl, 2,2 dimethyl cyclohexyl, cycloheptyl and the like.

By way of exemplification, the active thiolcarbamate herbicides employed in the invention may include the following: EPTC, S-ethyl diisobutyl thiolcarbamate, S-propyl dipropyl thiolcarbamate, S-2,3,3-trichloroallyldiisopropyl thiolcarbamate, S-ethyl cyclohexyl ethyl thiolcarbamate, S-ethyl hexahydro-1H-azepine-1-carbothioate, S-4-chlorobenzyl diethyl thiolcarbamate and combinations thereof.

The present invention also includes the method of selectively controlling undesirable vegetation in the presence of cultivated crops which comprises applying to a locus where control is desired an antidotally effective amount of a compound of the formula

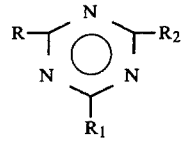

in which

R is selected from the group consisting of haloalkyl having 1-4 carbon atoms, preferably dichloromethyl or trichloromethyl, and alkylamino having 1-4 carbon atoms, preferably ethylamino and propylamino;

R₁ is selected from the group consisting of alkyl having 1-4 carbon atoms, preferably methyl, haloalkyl having 1-4 carbon atoms, preferably dichloromethyl, and chloro; and R₂ is selected from the group consisting of haloalkyl having 1-4 carbon atoms, preferably dichloromethyl and trichloromethyl, and N-dichloroacetylethylamino.

The thiolcarbamate herbicides are generally incorporated into the soil prior to planting. The antidote compound may be combined with the herbicide as a tank mix as it is incorporated into the soil. This is referred to as the "Pre-plant Incorporation" (PPI) Method of Application. The antidote may also be applied by the "In-furrow" (IF) Method of Application which consists of spraying the seeds and the herbicidally treated soil with the antidote compound prior to covering the seeds with soil.

Preparation

The thiolcarbamates of the present compositions can be prepared by the procedures described in U.S. Pat. Nos. 2,913,327, 2,983,747, 3,133,947, 3,185,720 and 3,198,786.

The s-triazines can be prepared by a variety of methods depending upon the starting materials. Tris-dichloromethyl-s-triazine and 2,6'-trichloromethyl-4'-methyl-s-triazine are commercially available.

The acetylamino-triazines may be prepared by the reaction of the appropriate aminotriazine and an acetyl chloride in a suitable solvent. The reaction is generally carried out at a temperature range of 50° to 150° C.

For example, 2-isopropylamino-4-chloro-6-(N-dichloroacetylethylamino)-s-triazine (Compound No. 4) was prepared in the following manner. 2-chloro-4-ethylamino-6-isopropylamino-s-triazine (5.4 grams (g)) or 0.025 mole (m), and 7.4 g (0.05 m) of dichloroacetyl chloride were combined in 50 milliliters (ml) of 1,2-dichloroethane. The mixture was refluxed for several hours, cooled and stripped, yielding 8.6 g of a dark viscous liquid which slowly crystallized (n$_D^{30}$ 1.5506). Structure was confirmed by infrared spectrophotometric analysis and nuclear magnetic resonance spectrum.

Table I contains representative s-triazine antidote compounds which were tested as part of the herbicidal compositions of this invention. Compound No. 1 can be found described in U.S. Pat. No. 2,525,714.

TABLE I

S-TRIAZINE HERBICIDAL ANTIDOTES

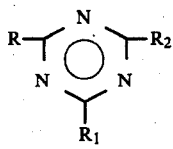

| Compound Number | R | $R_1$ | $R_2$ | Chemical Name | Physical Constant |
|---|---|---|---|---|---|
| 1 | $CHCl_2$ | $CHCl_2$ | $CHCl_2$ | Tris-dichloromethyl-s-triazine | m.p. 50–60° C. |
| 2 | $CCl_3$ | $CH_3$ | $CCl_3$ | 2',6'-trichloromethyl-4'-methyl-s-triazine | m.p. 88–90° C. |
| 3 | $NHC_2H_5$ | Cl | $\underset{C_2H_5}{\overset{\overset{\displaystyle O}{\|}}{NCCHCl_2}}$ | 2-ethylamino-4-chloro-6-(N-dichloroacetylethylamino)-s-triazine | $n_D^{30}$ 1.5312 |
| 4 | $\underset{NHCHCH_3}{CH_3}$ | Cl | $\underset{C_2H_5}{\overset{\overset{\displaystyle O}{\|}}{NCCHCl_2}}$ | 2-isopropylamino-4-chloro-6-(N-dichloroacetylethylamino)-s-triazine | $n_D^{30}$ 1.5312 |

Stock solutions of the various thiolcarbamate herbicides were prepared by dissolving the requisite amount of the herbicide in water.

Stock solutions of each antidote compound were prepared by dissolving the requisite amount in acetone. The herbicide and antidote compositions and their equivalent rates of application appear in Table II and III.

TABLE II

| Herbicidal Stock Solutions | | | |
|---|---|---|---|
| Composition | | Application | |
| Herbicide A (mg) | Water (ml) | ml soln | lb/A |
| EPTAM® S-ethyl-N,N-dipropyl thiolcarbamate | | | |
| 53 | 100 | 5 | 0.50 |
| 533 | 100 | 5 | 5.00 |

TABLE III

| Antidote Stock Solutions Antidote: s-triazines | | | |
|---|---|---|---|
| Composition | | Application | |
| Antidote (mg) | Acetone (ml) | ml soln | lb/A |
| Stock Solution A: | | | |
| 200 | 50 | 1.0 | 1.00 |
| 200 | 50 | 5.0 | 5.00 |
| Dilutions: | | | |
| 1 ml of A | 99 | 5.0 | 0.05 |

All of the soil used in the tests described herein was loamy sand soil treated with 50 parts per million (ppm) each of a commercially available fungicide, cis-N[trichloromethyl)thio]-4-cyclohexene-1,2-dicarboximide, and an 18-18-18 fertilizer which contains 18% by weight equivalent each of nitrogen, phosphorus pentoxide, and potassium oxide.

The herbicide and the antidote of each test group were pre-plant incorporated (PPI) into the treated soil. Control flats used for injury rating comparisons contained only the herbicide treated soil.

The flats were placed on greenhouse benches where temperature was maintained between 70° and 90° F. (21.11° to 32.22° C.). The soil was watered by sprinkling as needed to assure good plant growth.

Control flats contained crops treated with herbicides only at the various rates and methods of application.

Injury ratings were taken four weeks after application of the antidote. The effectiveness of the antidote was determined by visual comparison of injuries to crops and weeds in the control and test flats to those in untreated flats.

The treated crops initially screened for diminution of herbicidal injury were milo (*Sorghum bicolor* (L.) Moench), barley (*Hordeum vulgare* (L.)) and corn (*Zea mays* (L.)). The herbicides and antidote compositions were screened on the weed species, foxtail (*Setaria viridis*).

KEY TO TABLES IV AND V

Compound numbers in these tables correspond to antidote compound numbers and their chemical description in Table I.

| | | |
|---|---|---|
| Application: | PPI = | Pre-plant incorporation of herbicide and antidote |
| Herbicide: | | EPTAM® or S-ethyl N,N-dipropyl-thiolcarbamate, described in U.S. Pat. No. 2,913,327 |
| Rates: | | All rates are shown in pounds per acre |
| Injury Ratings: | U = | Antidotally untreated; % injury 4 weeks after herbicide application |
| | T = | Antidotally treated; % injury 4 weeks after treatment with herbicide plus antidote compound |
| | — = | Indicates no change |

TABLE IV

| Antidote Cmpd. No. | Rate | Method | Herbicide Name | Rate | Milo U | Milo T | Barley U | Barley T | Corn U | Corn T |
|---|---|---|---|---|---|---|---|---|---|---|
| 1 | 5.00 | PPI | EPTAM | 0.50 | 93 | — | 94 | — | | |
|   | 5.00 | PPI | EPTAM | 5.00 | | | | | 98 | 30 |
| 2 | 5.00 | PPI | EPTAM | 0.50 | 75 | 20 | 55 | 50 | | |
|   | 5.00 | PPI | EPTAM | 5.00 | | | | | 97 | 0 |
| 3 | 5.00 | PPI | EPTAM | 0.50 | 75 | — | 50 | 0 | 93 | — |
|   | 1.00 | PPI | EPTAM | 0.50 | | | 90 | 70 | | |
|   | 5.00 | PPI | EPTAM | 0.50 | | | 90 | 50 | | |
| 4 | 5.00 | PPI | EPTAM | 0.50 | 97 | 100 | 95 | 100 | | |
|   | 5.00 | PPI | EPTAM | 5.00 | | | | | 85 | 0 |

TABLE V

| Antidote Cmpd. No. | Rate | Method | Herbicide Name | Rate | % Weed Injury Foxtail U | % Weed Injury Foxtail T |
|---|---|---|---|---|---|---|
| 1 | 5.00 | PPI | EPTAM | 0.50 | 70 | — |
| 2 | 5.00 | PPI | EPTAM | 0.50 | 70 | — |
| 3 | 5.00 | PPI | EPTAM | 0.50 | 75 | — |
|   | 1.00 | PPI | EPTAM | 0.50 | 70 | — |
|   | 5.00 | PPI | EPTAM | 0.50 | 70 | — |
| 4 | 5.00 | PPI | EPTAM | 0.50 | 75 | 100 |
|   | 0.05 | PPI | EPTAM | 0.05 | 98 | — |

Formulations

The object of the formulation is to apply the compounds and compositions to the locus where control is desired by a conventional method. The "locus" may include soil, seeds, seedlings, and vegetation. The compounds and compositions can be formulated in the same manner in which herbicides are generally formulated.

The amount of an antidote compound which comprises part of a herbicidal composition will generally range from approximately 0.001 to 30 parts by weight per weight of the active herbicidal compound.

Formulations will generally contain several additives. Among these are some inert ingredients, diluent carriers, organic solvents, water, oil and water, water in oil emulsions, carriers of dusts and granules, and surface active wetting, dispersing, and emulsifying agents. Fertilizers, e.g., ammonium nitrate, urea and superphosphate, may also be included. Aids to rooting and growth, e.g., compost, manure, humus, sand, etc., may likewise be included. The formulations are commonly dusts, wettable powders, granules, solutions or emulsifiable concentrates.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anticaking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols; in which the alcohol groups are free, omega-substituted polyethylene glycols of relatively long chain length. A list of surface active agents suitable for use in agriculture formulations can be found in Wade Van Valkenburg, *Pesticide Formulations* (Marcel Dekker, Inc., N.Y., 1973) at pages 79–84.

Granules comprise the herbicidal composition impregnated on a particulate inert carrier having a particle size of about 1 to 2 millimeters (mm) in diameter. The granules can be made by spraying a solution of the active ingredient in a volatile solvent onto the granular carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of application permits the penetration of the compositions into the soil as the water is absorbed therein.

It is not necessary that the compounds and compositions be admixed with the soil particles. After application by the above discussed methods, they may be distributed below the surface to a depth of at least one-half inch by conventional means such as discing, dragging, or mixing.

We claim:
1. A herbicidal composition comprising
    (a) a non-phytotoxic antidotally effective amount for monocotyledon crops of a compound of the formula

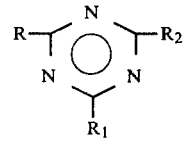

in which
- R is selected from the group consisting of haloalkyl having 1-4 carbon atoms and alkylamine having 1-4 carbon atoms;
- $R_1$ is selected from the group consisting of alkyl having 1-4 carbon atoms, haloalkyl having 1-4 carbon atoms, and chloro; and
- $R_2$ is selected from the group consisting of haloalkyl having 1-4 carbon atoms and N-dichloroacetylethylamino; and (b) a herbicidally effective amount of a thiolcarbamate of the formula

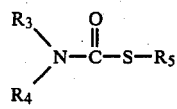

in which
- $R_3$ is selected from the group consisting of alkyl having 1-6 carbon atoms and alkenyl having 2-6 carbon atoms;
- $R_4$ is selected from the group consisting of alkyl having 1-6 carbon atoms, alkenyl having 2-6 carbon atoms, cyclohexyl and phenyl; or
- $R_3$ and $R_4$ together form a hexamethylene group;
- $R_5$ is selected from the group consisting of alkyl having 1-6 carbon atoms, haloalkyl having 1-4 carbon atoms, cycloalkyl having 5-10 carbon atoms, phenyl, substituted phenyl, wherein the substituents are alkyl having 1-4 carbon atoms, haloalkyl having 1-4 carbon atoms, and halo, benzyl, and substituted benzyl, wherein the substituents are alkyl having 1-4 carbon atoms, haloalkyl having 1-4 carbon atoms and halo.

2. A composition according to claim 1 in which $R_3$ and $R_4$ are each propyl and $R_5$ is ethyl.

3. A composition according to claim 2 in which R, $R_1$ and $R_2$ are each dichloromethyl.

4. A composition according to claim 2 in which R and $R_2$ are each trichloromethyl and $R_1$ is methyl.

5. A composition according to claim 2 in which R is alkylamino, $R_1$ is chloro, and $R_2$ is N-dichloroacetylethylamino.

6. A composition according to claim 5 in which R is ethylamino.

7. A composition according to claim 5 in which R is isopropylamino.

8. A method of controlling undesirable vegetation and reducing herbicidal injury to monocotyledon crops which comprises applying to the locus where control is desired a non-phytotoxic antidotally effective amount of a compound of the formula

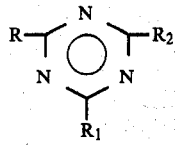

in which
- R is selected from the group consisting of haloalkyl having 1-4 carbon atoms and alkylamine having 1-4 carbon atoms;
- $R_1$ is selected from the group consisting of alkyl having 1-4 carbon atoms, haloalkyl having 1-4 carbon atoms, and chloro; and
- $R_2$ is selected from the group consisting of haloalkyl having 1-4 carbon atoms and N-dichloroacetylethylamino; and (b) a herbicidally effective amount of a thiolcarbamate of the formula

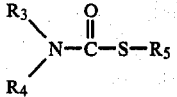

in which
- $R_3$ is selected from the group consisting of alkyl having 1-6 carbon atoms and alkenyl having 2-6 carbon atoms;
- $R_4$ is selected from the group consisting of alkyl having 1-6 carbon atoms, alkenyl having 2-6 carbon atoms, cyclohexyl and phenyl; or
- $R_3$ and $R_4$ together form a hexamethylene group; and
- $R_5$ is selected from the group consisting of alkyl having 1-6 carbon atoms, haloalkyl having 1-4 carbon atoms, cycloalkyl having 5-10 carbon atoms, phenyl, substituted phenyl, wherein the substituents are alkyl having 1-4 carbon atoms, haloalkyl having 1-4 carbon atoms, and halo, benzyl, and substituted benzyl, wherein the substituents are alkyl having 1-4 carbon atoms, haloalkyl having 1-4 carbon atoms and halo.

9. A method according to claim 8 in which R, $R_1$ and $R_2$ are each dichloromethyl.

10. A method according to claim 8 in which R and $R_2$ are each trichloromethyl and $R_1$ is methyl.

11. A method according to claim 8 in which R is alkylamino, $R_1$ is chloro, and $R_2$ is N-dichloroacetylethylamino.

12. A method according to claim 11 in which R is ethylamino.

13. A method according to claim 11 in which R is isopropylamino.

* * * * *